United States Patent [19]

Bognin et al.

[11] 4,257,772

[45] Mar. 24, 1981

[54] METHOD AND APPARATUS FOR CHEMICAL ANALYSIS OF SPECIMENS

[75] Inventors: Franco Bognin, San Bonifacio; Bruno Colombo, Cologno Monzesz, both of Italy

[73] Assignee: Carlo Erba Strumentazione S.p.A., Italy

[21] Appl. No.: 36,333

[22] Filed: May 7, 1979

[30] Foreign Application Priority Data

May 16, 1978 [IT]  Italy ................................ 23442 A/78

[51] Int. Cl.³ ...................... G01N 31/08; G06G 7/75; G01N 31/12
[52] U.S. Cl. ................... 23/230 PC; 23/232 C; 364/497; 422/80
[58] Field of Search ......... 422/80; 23/230 PC, 232 C; 364/497

[56] References Cited

U.S. PATENT DOCUMENTS

| | | | |
|---|---|---|---|
| 3,168,378 | 2/1965 | Maresh et al. | 23/230 PC UX |
| 3,241,922 | 3/1966 | Walisch | 422/80 |
| 3,518,059 | 6/1970 | Levy | 422/80 X |
| 3,732,411 | 5/1973 | Galeene | 364/497 |
| 3,838,969 | 10/1974 | Dugan | 23/230 PC |
| 3,861,874 | 1/1975 | Krc | 422/80 X |
| 3,880,587 | 4/1975 | Szakasits et al. | 23/230 PC |
| 4,106,908 | 8/1978 | Leplat-Gryspeerdt | 422/80 X |

*Primary Examiner*—Barry Richman
*Attorney, Agent, or Firm*—Lerner, David, Littenberg & Samuel

[57] ABSTRACT

A method and apparatus are disclosed for chemical analysis of specimens in order to detect the presence and percentages of given chemical elements (C, N, H, S and O) therein. Said specimen is subjected to known chemical treatments in order to reveal said elements, which elements are detected and revealed as peaks of a curve traced by the apparatus, each peak corresponding to an analyzed and detected element.

The surface area of each element peak is then correlated with that of the other element peaks in order to obtain a series of ratios between said areas.

Such ratios are then compared, for each element pairs, with an experimentally determined graph which is valuable for each element pair in all specimens and gives a ratio between the numbers of atoms of said element pair, so that from said ratios between the numbers of atoms of all analyzed and detected elements, a reduced formula of the specimen composition may be obtained. When the specimen is weighed, besides said reduced formula, it is possible to statistically locate a probable composition for the residue of the specimen molecule.

8 Claims, 3 Drawing Figures

METHOD AND APPARATUS FOR CHEMICAL ANALYSIS OF SPECIMENS

BACKGROUND OF THE INVENTION

1. Field of the Invention

This invention relates to a method and apparatus for carrying-out a chemical analysis on organic or inorganic compounds and substances, for instance in the field of pharmaceuticals and in all synthesis methods wherein microspecimens are to be chemically analyzed.

More specifically, this invention relates to a method and apparatus allowing to detect the presence of predetermined chemical elements, as C, N, H, S and O in the analyzed specimens, to obtain proportionality ratios between said elements and the percentage of each element within the whole specimen, as well as some indications to statistically determine elements or groups of elements that are present in the residue of the specimen molecule besides those specifically and individually detected.

2. Description of the Prior Art

The known prior art comprises analysis methods allowing the detection of the percentages of well defined chemical elements, usually the abovestated ones, within the whole specimen and then to obtain a so called "reduced formula", wherein the atomic ratios between said detected elements are given. The abovestated known methods always involve a weighing operation of the specimen to be analyzed, and then a series of chemical treatments on said specimen in order to determine and detect the presence of said elements. The apparatus gives an out-put curve having a sequence of peaks, each relating to a given element. This curve allows the obtaining of the desired results by calculating the areas as defined by each peak above a given "ground" level and correlating the value of each area with the specimen weight and with an experimental factor in order to obtain the percentage of the corresponding element in the analyzed specimen. In other words, for each chemical element, there is previously determined an experimental factor by which the following parameters are correlated: specimen weight, percentage of the element in the specimen and area of the related peak. Such factor is obtained by means of an analysis carried-out, under the same conditions, on standard specimens containing known element percentages. Thereafter, the analysis may be repeated on an unknown specimen and said factors are used in order to calculate the percentage of each element within said specimen.

However, such known systems show certain drawbacks that are avoided according to the present invention.

In particular, such known systems always require a previous weighing operation of the specimen to be analyzed, said operation involving a considerable loss of time, requiring highly qualified operators, introducing possible errors and resulting in an impossibility in some instances, for example when specimens having volatile substances are to be analyzed. Further, said known systems do not allow exploitation of the weighing operation in order to obtain further elements from the analysis and in particular to obtain a statistic location of the molecule portion not directly analyzed and detected.

OBJECTS OF THE INVENTION

Accordingly, an object of this invention is to provide an improved method and apparatus for carrying-out analyses of the type referred-to, wherein said "reduced formula" may be obtained without any specimen weighing operation. method and apparatus of the described type wherein, when specimen weighing operations are carried-out, a more complete determination of the molecule components is made and in particular a statistical location of the molecule "residual", i.e. the not directly detected elements.

SUMMARY OF THE INVENTION

The above and further objects are attained by a method comprising well known chemical treatments (for instance combustion or pyrolysis, reduction, gas-absorption, gas-chromatography treatments) on the specimen to be analyzed in order to obtain a curve wherein each of a number of predetermined elements within said specimen is defined by a peak above a preset "ground" level, said peaks involving an actual presence within the specimen of said well defined elements each of which is identified by the relative peak position as obtained by said specific element detecting chemical treatments, the improvement comprising the steps of obtaining values proportional to the single surface areas as defined by said peaks above said ground level, each value corresponding to a well defined chemical element; of correlating pairs of said values with each other in order to obtain first ratios between the values as obtained by integrating the peak surface areas corresponding to pairs of chemical elements; of obtaining second ratios from said first ratios, as a function of predetermined proportionality factors between said first ratios and the ratios between the numbers of atoms (atomic ratios) of each considered chemical element pair within the specimen, so to obtain a "reduced" formula of the analyzed substance or compound, wherein each element, the presence of which in the specimen has been detected by a peak having a discrete useful area, is identified in terms of a ratio between numbers of atoms of said element and another detected one so that a correlation between the numbers of atoms of all detected and analyzed chemical elements is obtained.

DESCRIPTION OF THE PREFERRED EMBODIMENTS

Figure 1:
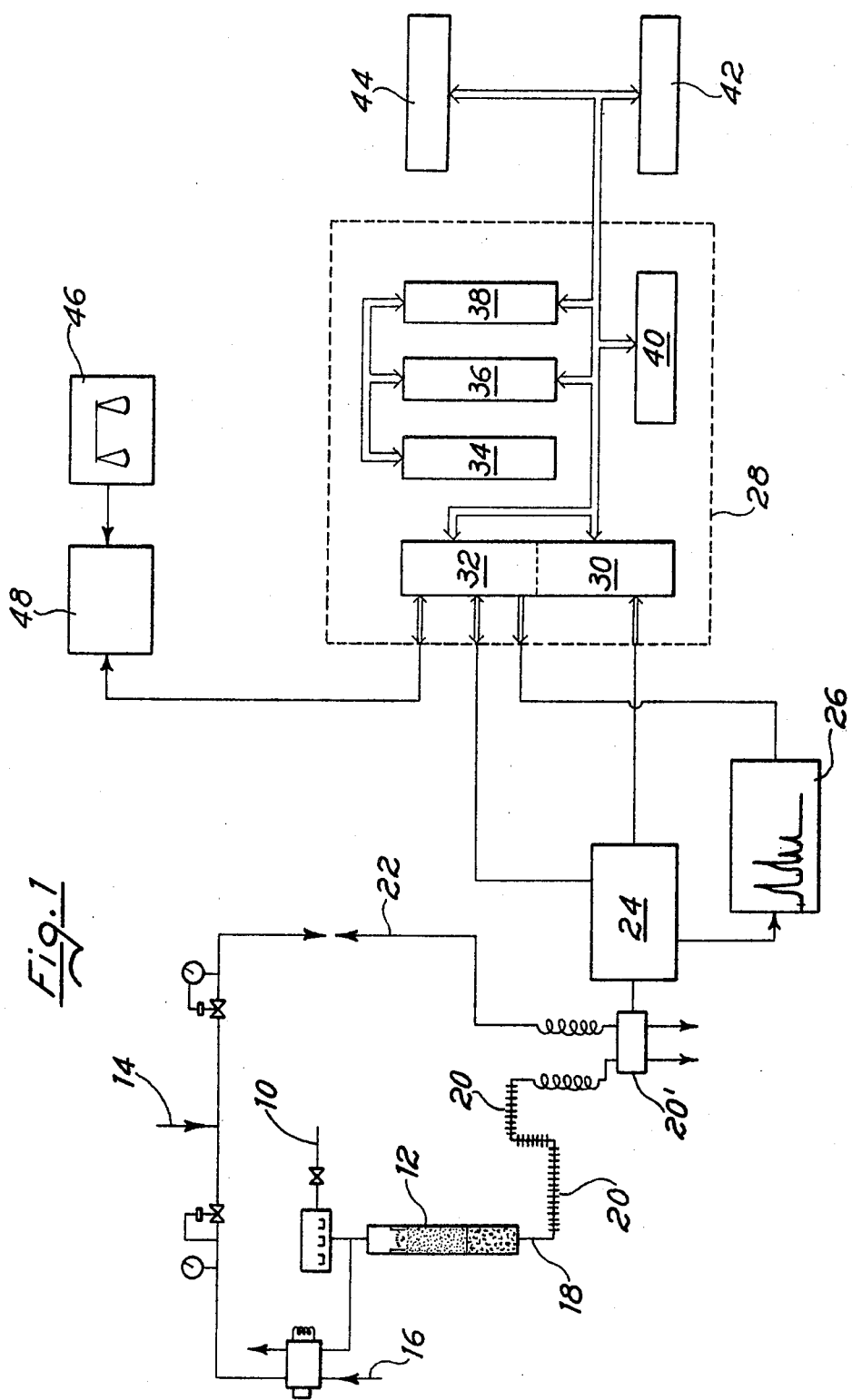
FIG. 1 is a diagrammatic view of an apparatus for carrying-out the method according to this invention.

Referring now to FIG. 1, the illustrated apparatus comprises a gas-chromatographic analyzer adapted to carry-out analyses on specimens which are introduced at 10 and fed to a reactor device 12 together with helium (fed at 14) and oxygen (at 16) in order to chemically treat the same and obtain an effluent 18 which is thermally conditioned at 20 and then fed to a thermoconductivity detector 20', together with a reference value, through line 22.

As well known, at the outlet of said thermoconductivity detector 20' a signal is obtained that is fed to a control unit wherein said signal is recorded at 26 and fed to a processing unit 28. This processing unit 28 comprises an analogic-to-digital convertor 30, an interface unit I/O 32, three units ROM 34, CPU 36 and RAM 38 and a computer unit 40. At the outlet, a control panel 42 and a display 44 for displaying the analysis results are provided for.

Said unit 28 may be fed with specimen weight data, which are detected by a balance 46 and fed to said interface unit I/O through a feeding unit 48.

Figure 2:
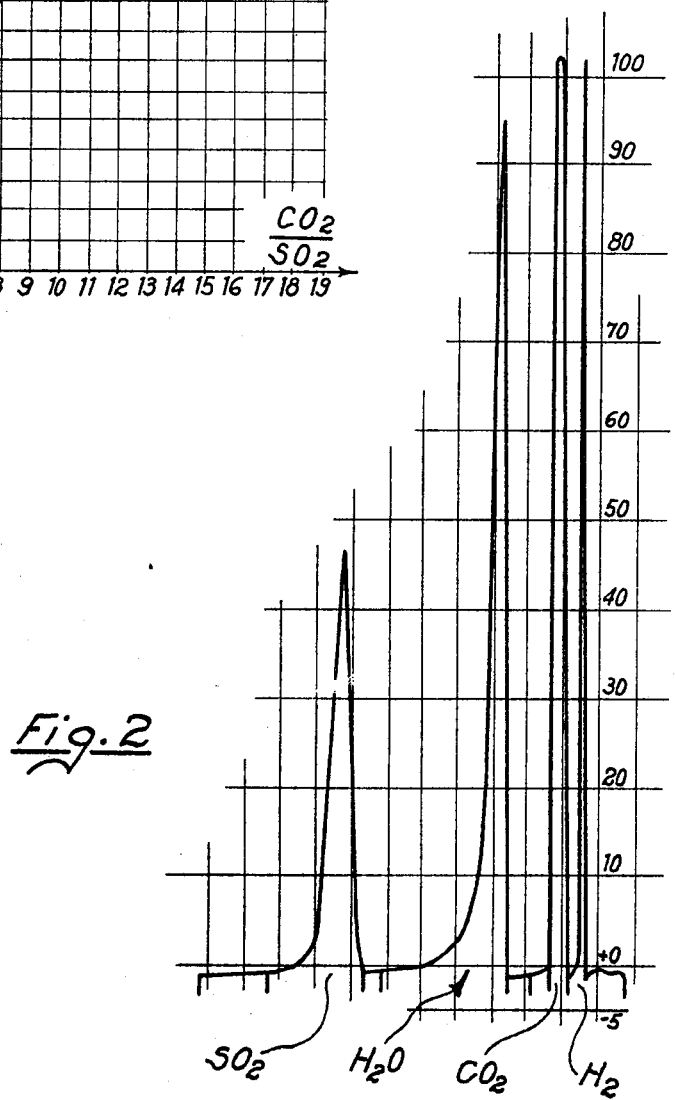
FIG. 2 is an example of a curve as obtained by chemically treating a specimen, said curve showing the presence of given chemical elements.

The electric signal, coming from said detector, is in the form of a curve showing a plurality of peaks, each of which represents a given chemical element, said curve being shown at 26 in FIG. 1 and more clearly, according to an example thereof, in the graph of FIG. 2, wherein the peaks respectively correspond, from the right side to the left one, to $N_2$, $CO_2$, $H_2O$ and $SO_2$. The first operating step as carried-out by the apparatus is an integration of said peaks, on the basis of given factors in order to take into account a "ground level" a "slope sensitivity" and a "lag time."

In other words, said integration is carried-out after definition of a ground level or "analytical white," as obtained by carrying-out a complete analytical procedure without a specimen. The value so obtained, which is referred to as "analytical white," is automatically determined and then subtracted to the integral value as obtained for each element in the specimen. This "analytic white" value may be also introduced by a keyboard on the control panel.

Another integration factor is that called "slope sensitivity" which can be automatically obtained and/or introduced by said keyboard in order to select the peaks to be integrated from possible curve slope variations, which variations are not due to the presence of a given chemical element.

Finally, said "lag time," which is the time elapsed from the analysis cycle and curve tracing starting point to the starting point of detection of a given specimen element, allows the identification of each specimen element by correlating said element with a given peak.

Said "lag time" may be automatically determined or introduced by said keyboard and, as it may vary, a further function "percentage change of lag time" is introduced by keyboard in order to always exactly identify each peak. The above integration may be carried-out by computer units as well known to those skilled in the art.

The values obtained by said integration are then processed by comparing the same both with each other and with experimentally obtained conversion factors in order to supply the required analysis results, i.e.: percentage of detected elements, reduced formula and probable composition of residual elements if the specimen has been weighed, or only reduced formula if the specimen weighing operation has not been carried-out.

More exactly, when the specimen is not weighed, it has been ascertained and experimentally confirmed that the ratios between said peak integrals are always proportional to the number of atoms of the detected elements within the specimen molecule, according to the formula:

$$R \frac{M}{N} = b \frac{AM}{AN} + a$$

wherein R is the required ratio between the numbers of atoms of two given elements M and N, AM and AN are the peak integral values relating to said elements M and N and calculated as previously stated, and a and b are the coefficients of a straight line (in a graph AM/AN; R(M/N)) which can be experimentally obtained once and introduced into the analyzer unit. The above formula is shown as an example in FIG. 3 wherein a graph relating to the ratios between elements C and S is depicted. More exactly the abscissae of said graph show the ratios between peak surface areas or integrals for $CO_2/SO_2$, while the ordinates show the C/S atom number ratios. For instance, if the ratio $CO_2/SO_2$ is 9 in the analyzed specimen, according to said graph of FIG. 3, the atomic ratio C/S is 10, i.e. the analyzed specimen has ten carbon atoms for each sulphur atom. A graph of the type shown in FIG. 3 may be experimentally obtained for each chemical element pair from a series of known specimens, said graph being then introduced into the apparatus store in order to allow a data processing by comparing each element pair peak ratio with one of said graphs.

The above method according to this invention has been used, in order to verify the precision thereof, on non-weighed specimens of well known substances, according to the following examples:

EXAMPLE 1

Benzoic Acid $C_7H_6O_2$

Figure 3:
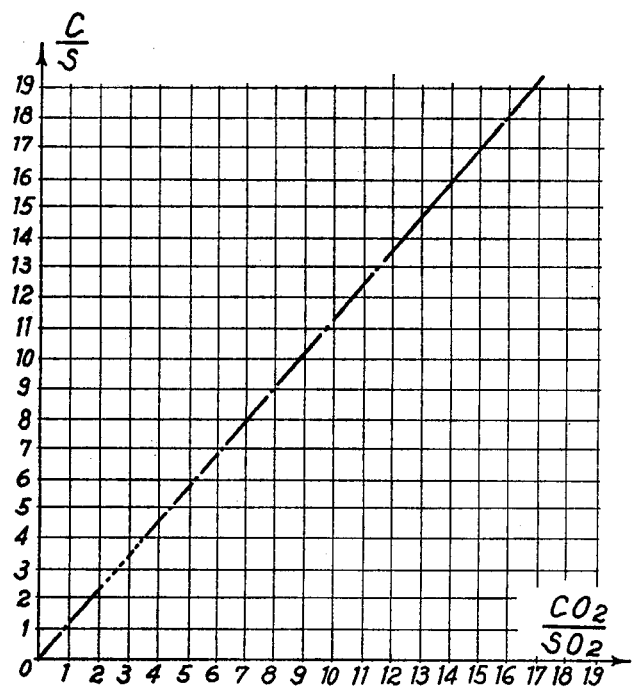
FIG. 3 is a graph showing the correlation between the ratios of the peak areas relating to two chemical elements and the atomic ratios between the same elements.

The peak integral values are:
$CO_2 = 1002725$
$H_2O = 239942$
The area or integral value ratio is: $CO_2/H_2O = 1002725/239942 = 4.18$ By means of a graph C/H of the type as shown in FIG. 3 the atomic ratio C/H may be determined.

According to said graph, said value 4.18 (peak ratio) corresponds to a value 1.17 (atomic ratio), i.e. each H atom corresponds to 1.17 C atoms and then the reduced formula may be $C_7H_6$.

EXAMPLE 2

Isatin $C_8H_5NO_2$

The peak integration values are:
$N_2 = 43651$; $CO_2 = 797436$; $H_2O = 140985$
The integral ratios are:
$CO_2/N_2 = 797436/43651 = 18.27$
$CO_2/H_2O = 797436/140985 = 5.66$ On a graph C/N it may be ascertained that a value 18.27 (integral ratio) corresponds to a value 8 (atomic ratio) and then that 8 carbon atoms are present in the specimen for each nitrogen atom.

On a graph C/H it may be ascertained that a value 5.66 (integral ratio) corresponds to a value 1.60 (atomic ratio) and then that 1.60 carbon atoms are present in the specimen for each hydrogen atom ($C_8H_5$ or $C_{16}H_{10}$...).

Accordingly, the reduced formula is $C_8H_5N$.

EXAMPLE 3

Cystine $C_6H_{12}N_2O_4S_2$

Peak integral values:
$N_2 = 63174$; $CO_2 = 445570$; $H_2O = 244989$; $SO_2 = 172162$.
Integral ratios:
$CO_2/N_2 = 445570/63174 = 7.05$ $CO_2/H_2O = 445570/244989 = 1.82$ $CO_2/SO_2 = 445570/172162 = 2.59$ To value 7.05 (integral ratio) corresponds a value 3 (atomic ratio), i.e. for each N atom the molecule contains 3C atoms ($N_nC_{3n}$)

To value 1.82 (integral ratio) corresponds a value 0.50 (atomic ratio), i.e. for each C atom the molecule contains 2H atoms ($C_nH_{2n}$)

To value 2.59 (integral ratio) corresponds a value 3 (atomic ratio—graph of FIG. 3), i.e. for each S atom the molecule contains 3C atoms ($S_nC_{3n}$).

Accordingly, the reduced formula is $(C_3H_6NS)_n$.

From the above examples and from what precedes it is now evident that the illustrated method has some advantages with reference to known methods and namely it allows the determination of specimen without weighing operations, without the influence of any organic residual on the ratios, without the influence of volatile substance losses during weighing and without any difficulty for weighing liquid substances.

Further, it allows the obtaining of good results also when volatile substances are analyzed and the reduction of the analysis time.

As previously stated, the apparatus according to this invention allows also for the carrying out of an analysis wherein the specimen weight W is introduced. In such a case, the apparatus processes the conversion factors on the basis of standard specimens having a known content, which are subjected to the same analysis as the examined specimens. For each standard specimen and for each chemical element a conversion factor may be obtained, as follows:

$$Ki1 = (W1\ Pi1\%)/Ai1$$

wherein:

Ki1 = conversion factor of element i within standard specimen 1

W1 = weight of standard specimen 1

Ai1 = surface area of the peak relating to element i within standard specimen 1

Pi1% = Known percentage of element i within standard specimen 1.

For each element i, different factors kl are statistically processed in order to obtain an average factor ki. From such average factor ki and from the peak integral values of the elements within the analyzed specimen, it is possible to obtain the percentages of each element within said analyzed specimen:

$$Pi\% = \frac{Ki\ Ai}{W}$$

wherein

Pi% = percentage of element i within the analyzed specimen

W = weight of the analyzed specimen

Ai = integral value of the peak relating to element i within the analyzed specimen.

From the knowledge of the chemical element atomic weights Pa, the following ratios are obtained:

$$i = (Pi\%)/(Pai)$$

wherein i = C, H, N and S

The minimum value i min between the above ratios allow the obtaining of the required atomic ratios, one of which is of course 1:

$$C = \frac{iC}{i\min} \quad H = \frac{iH}{i\min} \quad N = \frac{iN}{i\min} \quad S = \frac{iS}{i\min}$$

in order to obtain the specimen reduced formula.

Always with weighed specimens, it is possible to obtain the molecule residual R, i.e. the difference from 100:

$$100 - \epsilon i\ Pi\% = R$$

Such value allows the obtaining of indications on the probable molecule residual contents, on the basis of a number x which is equal to the number of atoms times the atomic weight of the elements forming said molecule remainder:

$$R:100 = x:(M+x)$$

wherein $M = \epsilon ni\ Pai$ ni = number of atoms of the analyzed elements

Pai = atomic weight of the analyzed elements

Accordingly $R:(100-R) = x:(M+x-x)$ $R:\epsilon i\ Pi\% = x:M$ $x = (RM)/(\epsilon i\ Pi\%)$ The following experimental table allows the identification of a probable composition of the molecule remainder.

From what precedes it is now evident that a new method is provided according to this invention, allowing the carrying out of both the analysis of specimens without weighing operations and a more complete analysis of weighed specimens with reference to preceding analysis methods of weighed specimens. It is to be understood that various changes and modifications may be introduced by those skilled in the art, without departing from the spirit and scope of the present invention.

TABLE

| | | | | | |
|---|---|---|---|---|---|
| 16 | O | 66.42 | PCl | 95 | $F_5$ |
| 19 | F | 67 | $O_3F$ | 95.91 | OBr |
| 23 | Na | 67.45 | $O_2Cl$ | 98.91 | FBr |
| 30.97 | P | 70 | $F_2O_2$ | 99.45 | $O_4Cl$ |
| 32 | $O_2$ | 70.90 | $Cl_2$ | 101.87 | PCl |
| 35 | OF | 71 | $O_3Na$ | 102.90 | $O_2Cl_2$ |
| 35.45 | Cl | 76 | $F_4$ | 103 | $O_5Na$ |
| 38 | $F_2$ | 77.94 | $P_2O$ | 106.35 | $Cl_3$ |
| 39 | ONa | 78 | $O_2Na_2$ | 108.90 | $F_2Cl_2$ |
| 46.97 | PO | 78.97 | $PO_3$ | 110.97 | $PO_6$ |
| 48 | $O_3$ | 79.91 | Br | 111.91 | $O_2Br$ |
| 51 | $O_2F$ | 83 | $O_4F$ | 114 | $F_6$ |
| 51.45 | OCl | 83.45 | $O_3Cl$ | 115.36 | ClBr |
| 54 | $OF_2$ | 86 | $O_3F_2$ | 115.45 | $O_5Cl$ |
| 54.45 | ClF | 86.91 | $OCl_2$ | 117.91 | $F_2Br$ |
| 55 | $O_2Na$ | 87 | $O_4Na$ | 118.91 | $O_3Cl_2$ |
| 57 | $F_3$ | 89.90 | $FCl_2$ | 122.36 | $OCl_3$ |
| 58.45 | NaCl | 93.90 | $Cl_2Na$ | 126.90 | I |
| 62.97 | $PO_2$ | 93.94 | $P_2O_2$ | 126.97 | $PO_6$ |
| 64 | $O_4$ | 94.97 | $PO_4$ | 127.91 | $O_3Br$ |

We claim:

1. A method for determining the reduced atomic ratios of C, N, H and S in a substance, said method comprising (1) decomposing the substance into compounds corresponding respectively to the C, N, H and S atoms in such substance; (2) separating said compounds; (3) detecting the respective amount of each separated compound and providing continuous outputs whose values form a curve having peaks defining an area thereunder, said peaks having positions along said curve identifying the compounds and said area under each identifying peak defining the amount of the compound represented by each identifying peak; (4) determining the area under each identifying peak to obtain an experimental area value for each compound, (5) storing said experimental area values in a memory; (6) selectively reading out pairs of said experimental area values from said memory; (7) determining experimental area ratios from said pairs of experimental area values; (8) storing predetermined correlations between (a) predetermined ratios of peak areas for pairs of said compounds and (b) reduced atomic ratios representing the ratios of the numbers of C, N, H or S atoms in said pairs of said compounds; and (9) determining the experimental reduced atomic ratio of the number of C, N, H and S atoms in said substance from said experimental area ratios and said stored predetermined correlations.

2. The method of claim 1, wherein the detection of the respective amount of each separated compound is accomplished by a thermoconductivity detector attached to a gas chromatographic column, which column is used to separate the compounds.

3. A method according to claim 1, wherein said separating is accomplished by gas-chromatography.

4. A method according to claim 1, wherein said predetermined correlations are obtained from a previously and experimentally obtained curve, wherein the peak area ratios are correlated with said atomic ratios for each detectable chemical element pair.

5. A method according to claim 4, wherein said experimentally obtained curve is a straight line.

6. An apparatus for determining the reduced atomic ratios of C, N, H and S in a substance, said apparatus comprising (1) means for decomposing the substance into compounds corresponding respectively to the C, N, H and S atoms in such substance; (2) means for separating said compounds; (3) means for detecting the respective amount of each separated compound and providing continuous outputs whose values form a curve having peaks defining an area thereunder, said peaks having positions along said curve identifying the compounds and said area under each identifying peak defining the amount of the compound represented by each identifying peak; (4) means for determining the area under each identifying peak to obtain an experimental area value for each compound, (5) memory means for storing said experimental area values in said memory means; (6) means for selectively reading out pairs of said experimental area values from said memory means; (7) means for determining experimental area ratios from said pairs of experimental area values; (8) read only memory means for storing predetermined correlations between (a) predetermined ratios of peak areas for pairs of said compounds and (b) reduced atomic ratios representing the ratios of the numbers of C, N, H, or S atoms in said pairs of said compounds; and (9) means, responsive to said means for determining experimental area ratios and to said read only memory means, for determining the experimental reduced atomic ratio of the number of C, N, H and S atoms in said substance from said experimental area ratios and said predetermined correlations.

7. An apparatus according to claim 6, wherein said means for separating is a gas chromatography apparatus.

8. An apparatus according to claim 6, wherein said means for separating said compounds comprises a gas chromatographic column and said means for detecting comprises a thermoconductivity detector attached to said gas chromatographic column for detection of separated compounds passing through said column, said thermoconductivity detector cooperating with a control unit and a recorder so that the output values from said thermoconductivity detector for each separated compound are graphically displayed as a peak above a predetermined ground value.

* * * * *

UNITED STATES PATENT AND TRADEMARK OFFICE
CERTIFICATE OF CORRECTION

PATENT NO. : 4,257,772
DATED : March 24, 1981
INVENTOR(S) : Franco Bognin and Bruno Colombo It is certified that error appears in the above-identified patent and that said Letters Patent are hereby corrected as shown below:

Column 2, line 7, after "operation." insert --Another object of this invention is to provide an improved--.

*Signed and Sealed this*

*Sixteenth* Day of *June 1981*

[SEAL]

*Attest:*

RENE D. TEGTMEYER

*Attesting Officer*     *Acting Commissioner of Patents and Trademarks*